US007196246B2

(12) United States Patent
Yano et al.

(10) Patent No.: US 7,196,246 B2
(45) Date of Patent: Mar. 27, 2007

(54) *HD3A* GENE INDUCING FLOWERING OF PLANT AND UTILIZATION THEREOF

(75) Inventors: Masahiro Yano, Ibaraki (JP); Shoko Kojima, Aichi (JP)

(73) Assignees: National Agriculture and Bio-oriented Research Organization, Ibaraki (JP); National Institute of Agrobiological Sciences, Ibaraki (JP); Society for Techno-Innovation of Agriculture, Forestry and Fisheries, Tokyo (JP)

( * ) Notice: Subject to any disclaimer, the term of this patent is extended or adjusted under 35 U.S.C. 154(b) by 146 days.

(21) Appl. No.: 10/432,531

(22) PCT Filed: Nov. 22, 2001

(86) PCT No.: PCT/JP01/10237

§ 371 (c)(1),
(2), (4) Date: Oct. 2, 2003

(87) PCT Pub. No.: WO02/42475

PCT Pub. Date: May 30, 2002

(65) Prior Publication Data

US 2004/0088763 A1    May 6, 2004

(30) Foreign Application Priority Data

Nov. 24, 2000    (JP)    ............................. 2000-356839

(51) Int. Cl.
*C12N 15/29*    (2006.01)
*C12N 15/82*    (2006.01)
*C12N 5/04*    (2006.01)
*A01H 5/00*    (2006.01)

(52) U.S. Cl. ...................... 800/290; 800/278; 800/298; 800/320.2; 800/260; 536/23.1; 536/23.6; 435/320.1; 435/419

(58) Field of Classification Search ............... 536/23.1, 536/23.6; 800/278, 298, 290, 320.2; 435/320.1, 435/419, 468
See application file for complete search history.

(56) References Cited

U.S. PATENT DOCUMENTS 6,025,544 A * 2/2000 Leggewie et al. .......... 800/290

FOREIGN PATENT DOCUMENTS

| WO | WO 97/10339 A1 | 3/1997 |
| WO | WO 99/53070 A1 | 10/1999 |
| WO | WO 00/71722 A1 | 11/2000 |

OTHER PUBLICATIONS

Kobayashi et al (1999, Science, 286:1960-1962).*
Kano-Murakami et al (1993, FEBS 334:365-368).*
Bowie et al, Science 247:1306-1310, 1990.*
McConnell et al, Nature 411 (6838):709-713, 2001.*
Fourgoux-Nicol et al (1999, Plant Molecular Biology 40 :857-872).*
He, Z., et al., "Transformation of rice with the *Arabidopsis* floral regulator *LEAFY* causes early heading," *Transgenic Res.* 9:223-227, Kluwer Academic Publishers (Jun. 2000).
Lin, H.X., et al., "Characterization and detection of epistatic interactions of 3 QTLs, *Hd1*, *Hd2*, and *Hd3*, controlling heading date in rice using nearly isogenic lines," *Theor. Appl. Genet.* 101:1021-1028, Springer-Verlag (Nov. 16, 2000).
Yano, M., and Sasaki, T., "Genetic and molecular dissection of quantitative traits in rice," *Plant Mol. Biol.* 35:145-153, Kluwer Academic Publishers (1997).
Altschul, S.F., et al., "Basic Local Alignment Search Tool," *J. Mol. Biol.* 215:403-410, Academic Press Ltd. (1990).
Buzayan, J.M., et al., "Non-enzymatic cleavage and ligation of RNAs complementary to a plant virus satellite RNA," *Nature* 323:349-352, Macmillan Publishers (1986).
Christou, P., et al., "Production of Transgenic Rice (*Oryza Sativa L.*) Plants from Agronomically Important Indica and Japonica Varieties Via Electric Discharge Particle Acceleration of Exogenous DNA Into Immature Zygotic Embryos," *Bio/Tech* 9:957-962, Nature Publishing Group (1991).
Ecker, J.R. and Davis, R.W., "Inhibition of gene expression in plant cells by expression of antisense RNA," *Proc. Natl. Acad. Sci. USA* 83:5372-5376, National Academy of Sciences (1986).
Dzianott, A.M. and Bujarski, J.J., "Derivation of an infectious viral RNA by autolytic cleavage of *in vitro* transcribed viral cDNAs," *Proc. Natl. Acad. Sci. USA* 86 :4823-4827, National Academy of Sciences (1989).
Grosshans, C.A. and Cech, T.R., "A hammerhead ribozyme allows synthesis of a new form of the *Tetrahymena ribozyme* homogenous in length with a 3' end blocked for transesterification," *Nucl. Acids Res. 19*: 3875-3880, Oxford University Press (1991).
Hiei, Y., et al., "Efficient transformation of rice (*Oryza sativa* L. ) mediated by *Agrobacterium* and sequence analysis of the boundaries of the T-DNA," *Plant J.* 6:271-282, Blackwell Scientific Publishers and BIOS Scientific Publishers in association with the Society for Experimental Biology (1994).
Karlin, S. and Altschul, S.F., "Applications and statistics for multiple high-scoring segments in molecular sequences," *Proc. Natl. Acad. Sci. USA* 90:5873-5877, National Academy of Sciences (1993).
Kikuchi, Y. and Sasaki, N., "Site-specific cleavage of natural mRNA sequences by newly designed hairpin catalytic RNAs," *Nucl. Acids Res.* 19:6751-6755, Oxford University Press (1991).
Kobayashi, Y., et al., "A Pair of Related Genes with Antagonistic Roles in Mediating Flowering Signals," *Science* 286:1960-1962, American Association for the Advancement of Science (Dec. 1999).
Koizumi, M., et al., "Construction of a series of several self-cleaving RNA duplexes using synthetic 21-mers," *FEBS Lett.* 228:228-230, Elsevier Science Publishers B.V. (1988).

(Continued)

*Primary Examiner*—Stuart F. Baum
(74) *Attorney, Agent, or Firm*—Sterne, Kessler, Goldstein & Fox P.L.L.C.

(57) ABSTRACT

By linkage analysis, the Hd3a gene was successfully isolated. It was discovered that the flowering time of plant could be modified either by introducing the Hd3a gene or by controlling its expression.

12 Claims, 4 Drawing Sheets

OTHER PUBLICATIONS

Koizumi, M., et al., "Cleavage of specific sites of RNA by designed ribozymes," *FEBS Lett. 239*:285-288, Elsevier Science Publishers B.V. (1988).

Koizumi, M., et al., "Design of RNA enzymes distinguishing a single base mutation in RNA," *Nucl. Acids Res. 17*:7059-7091, Oxford University Press (1989).

Kramer, W. and Fritz, H.-J., "Oligonucleotide-Directed Construction of Mutations via Gapped Duplex DNA," *Meth. Enyzmol. 154*:350-367, Academic Press Inc. (1987).

Martienssen, R., "Epigenetic phenomena: Paramutation and gene silencing in plants," *Curr. Biol. 6*:810-813, Current Biology Ltd. (1996).

Saiki, R.K., et al., "Enzymatic Amplification of β-Globin Genomic Sequences and Restriction Site Analysis for Diagnosis of Sickle Cell Anemia," *Science 230*:1350-1354, American Association for the Advancement of Science (1985).

Saiki, R.K., et al., "Primer-Directed Enzymatic Amplification of DNA with a Thermostable DNA Polymerase," *Science 239*:487-491, American Association for the Advancement of Science (1988).

Smyth, D. R., "Gene silencing: Cosuppression at a distance," *Curr. Biol.* 7:R793-R795, Current Biology (1997).

Southern, E.M., "Detection of Specific Sequences Among DNA Fragments Separated by Gel Electrophoresis," *J. Mol. Biol. 98*:503-517, Academic Press (1975).

Taira, K., et al., "Construction of a novel artificial-ribozyme-releasing plasmid," *Protein Eng. 3*:733-737, Oxford University Press (1990).

Taira, K., et al., "Construction of a novel RNA-transcript-trimming plasmid which can be used both *in vitro* in place of run-off and (G) -free transcriptions and *in vivo* as multi-sequences transcription vectors," *Nucl. Acids Res. 19*:5125-5130, Oxford University Press (1991).

Toki, S., et al., "Expression of a Maize Ubiquitin Gene Promoter-bar Chimeric Gene in Transgenic Rice Plants," *Plant Physiol. 100*:1503-1507, American Society for Plant Physiologists (1992).

Tsai, K.-H., "Studies on Earliness Genes in Rice, With Special Reference to Analysis of Isoalleles at the *E* Locus," *Japan J. Genet.* 51:115-128, Genetics Society of Japan (1976).

van der Krol, A.R., et al., "An anti-sense chalcone synthase gene in transgenic plants inhibits flower pigmentation," *Nature 333*:866-869, Macmillan Publishers (1988).

Yamagata, H., et al., "Analysis of Genes Controlling Heading Time in Japanese Rice," *Rice Genetics: Proceedings of the International Rice Genetics Symposium*, Manila, Philippines, pp. 351-359, International Rice Research Institute (1986).

Yokoo, M. and Fujimaki, H., "Tight Linkage of Blast-Resistance with Late Maturity Observed in Different *Indica* Varieties of Rice," *Japan. J. Breed.* 21:35-39, Nihon Ikushu Gakkai (1971).

Yuyama, N., et al., "Construction of a tRNA-embedded-ribozyme trimming plasmid," *Biochem. Biophys. Res. Comm. 186*:1271-1279, Academic Press, Inc. (1992).

English language abstract of Kikuchi, Y., "Ribozymes: Types and *in vivo* Activity- hammerhead and hairpin ribozymes," *Chem. & Biol. (Kagaku To Seibutsu)* 30:112-118 (1992) (Document AR4), abstract only.

English language abstract of Koizumi, M. and Ohtsuka, E., "Ribozyme for Sequence-dependent Cleavage of Target RNA," *Nucl. acid, Prot., Enzyme* (*Tanpakushitsu Kakusan Kohso*) 35:2191-2200, Tokyo Kyoritsu Shuppan Co. (1990) (Document AT5), abstract only.

Okumoto, Y., et al., "Analysis of a Rice Variety Taichung 65 and Its Isogenic Early-heading Lines for Late-heading Genes $E_1$, $E_2$, and $E_3$," *Japan. J. Breed 42*:415-429, Nihon Ikushu Gakkai (1992), English summary only.

Unverified English translation of JP 2000-139250 A, document AM2, May 2000.

Unverified English translation of WO 01/32881 A1, document AN2, May 2001.

Unverified English translation of WO 03/100062 A1, document AO2, Dec. 2003.

Kyozuka, J., et al., "Down-regulation of *RFL*, the *FLO/LFY* homolog of rice, accompanied with panicle branch initiation," *Proc. Natl. Acad. Sci. USA 95*:1979-1982, National Academy of Sciences (1988).

* cited by examiner

SEQUENCE LISTING

```
<160> NUMBER OF SEQ ID NOS: 24

<210> SEQ ID NO 1
<211> LENGTH: 4229
<212> TYPE: DNA
<213> ORGANISM: Oryza sativa
<220> FEATURE:
<223> OTHER INFORMATION: genomic DNA
<220> FEATURE:
<221> NAME/KEY: exon
<222> LOCATION: (825)..(1184)
<220> FEATURE:
<221> NAME/KEY: intron
<222> LOCATION: (1185)..(1346)
<220> FEATURE:
<221> NAME/KEY: exon
<222> LOCATION: (1347)..(1408)
<220> FEATURE:
<221> NAME/KEY: intron
<222> LOCATION: (1409)..(1541)
<220> FEATURE:
<221> NAME/KEY: exon
<222> LOCATION: (1542)..(1582)
<220> FEATURE:
<221> NAME/KEY: intron
<222> LOCATION: (1583)..(2889)
<220> FEATURE:
<221> NAME/KEY: exon
<222> LOCATION: (2890)..(3274)
<220> FEATURE:
<221> NAME/KEY: CDS
<222> LOCATION: (978)..(1184)
<220> FEATURE:
<221> NAME/KEY: CDS
<222> LOCATION: (1347)..(1408)
<220> FEATURE:
<221> NAME/KEY: CDS
<222> LOCATION: (1542)..(1582)
<220> FEATURE:
<221> NAME/KEY: CDS
<222> LOCATION: (2890)..(3119)

<400> SEQUENCE: 1
gataagttgc ggaaaaacca acaaattagc aacaaatatg agtaaaactt gtatacatgt      60
gtcttcttag cgatttaaaa atcaatgctg aaaataaatt ataataaaat taaaaatctc     120
aagataatct ctaaaatgta gttttaaaat ttaaattttg attgcgactg ataagaaaaa     180
aaaacaaatg atgggaggct atatcaactg tcaaactggc taatttagaa agacgacatc     240
gaattcctac agattggagg cagcaaaaga gagcctgtct ctgccgggtg cgtgcatgat     300
gctcgatcat atcccatctc tcctcacttc atcatcaaca agaacaagag gaactatata     360
gctgcaagat ctagactgaa actactatag caactaactg tactgtagct agattacgct     420
```

```
tagctatagc tgctgctgca gctgctgctg catctatctg taaattccaa ctacgacgtc    480
gactgctgca agctagcttg accggctagc tagatagcta gctagctcaa aagagaaagc    540
tttgcgaaat aggagtagct agctagctct agctagggcg ccatcgatgc gtgaccaccg    600
agctcgcctc gtccacacgt acaggaagac gatgcagaaa gcggccggca tgcagtaaac    660
tgaccgagct aagagagaga gagagagatg atattattct tctgcagcta aattaaagtg    720
aaagttggac atggacatgg acatagtaat tttgcatggc catcatcttg ccctcctata    780
taaagcggcc atctcactct caaccacagc tcgatccagc agccctgcac cacacacagt    840
tcagctagca gatcacctag ctagatagct gcctctatca cagtatattt gctccctgca    900
acttgctgct gctgcaatag ctagcagctg cagctagtaa gcaaaactat ataccttcag    960
ggttttttgc aagatcg atg gcc gga agt ggc agg gac agg gac cct ctt     1010
              Met Ala Gly Ser Gly Arg Asp Arg Asp Pro Leu
                1          5                    10 gtg gtt ggt agg gtt gtg ggt gat gtg ctg gac gcg ttc gtc cgg agc    1058
Val Val Gly Arg Val Val Gly Asp Val Leu Asp Ala Phe Val Arg Ser
         15                  20                  25 acc aac ctc aag gtc acc tat ggc tcc aag acc gtg tcc aat ggc tgc    1106
Thr Asn Leu Lys Val Thr Tyr Gly Ser Lys Thr Val Ser Asn Gly Cys
     30                  35                  40 gag ctc aag ccg tcc atg gtc acc cac cag cct agg gtc gag gtc ggc    1154
Glu Leu Lys Pro Ser Met Val Thr His Gln Pro Arg Val Glu Val Gly
 45                  50                  55 ggc aat gac atg agg aca ttc tac acc ctt gtatgtgagc tctaccatgt      1204
Gly Asn Asp Met Arg Thr Phe Tyr Thr Leu
 60                  65 gtcgtagttg gttcagagac cagaagttat actttctttc attattatat tgtagaaaat    1264
tttgtttggt acttaaccca agatgacttt aaaatgcatt aatttgatgt ttgtcatggt    1324
tgtttgtggt gtgtacctga ag gtg atg gta gac cca gat gca cca agc cca    1376
                       Val Met Val Asp Pro Asp Ala Pro Ser Pro
                         70                  75 agt gac cct aac ctt agg gag tat cta cat tg gtaagcacac taatgttaag    1428
Ser Asp Pro Asn Leu Arg Glu Tyr Leu His Trp
 80                  85                  90 ctagcgcact tgttttcatg caatgatcaa ataatcact gctagctgat ttacatacat     1488
aaccacatct tgactgcatg atgggttgat catcttaatt tgtttgtcca cag g ttg    1545
                                                             Leu gtc act gat att cct ggt act act gca gcg tca ttt g gtcagtatta        1592
Val Thr Asp Ile Pro Gly Thr Thr Ala Ala Ser Phe
 95                  100 aacgatcaaa tggtttagat tgatttgatt tcccacttaa atacattgca gtataaaact    1652
aacagaggta aattgtcttt ccatactatt gtttgggggg ggggggggg ggcagtgagt    1712 tgttgagcat tttccctcac tcgcgagccc ccagtttgcc gcattaattc ccatcatcc    1772 ttcaccacca ccaaaaataa aaagtgattt ggagaaggat acgctcctcc aaataatttt    1832
taacaagttc accaccacaa cgaggcaccg ataaccgcca tgagtccacg caccctgcag    1892
ctagtcgtgc caccagcacc acagtttgcc acaccgcgag caatccacgc catcacttgc    1952
cgctgtgagt ccacgatcac acgcctcgat cagccagctg ccatgatatg tcggcttggg    2012
cttggattcc gcaacatacc atgtccccat cgatggcacc acactctaat tcgccaacac    2072
aacactgaag ggatcggacc gggagggcta gctcactcaa gatagtgacg ggatgattcg    2132
atgggaattc catggggaac aaagcacaaa atcatgaaaa tgtccttttc aattccatgg    2192
```

```
caaattccta aagcaatact ctctctccat tctataatgt aggttgcaca ctcatttcaa    2252
gattcaactt tcaaaacatt tgactaacga tttgtataat ataaattgaa ttttatttga    2312
tagaaataat attattggat tgatatttca atatactttc atatggttat aattttgtta    2372
ctacaaactt tatagtatat tagaaattat aaataaaaaa ttagttttat agaccgtaca    2432
tgccaagttt gaccatacca taatatgaaa agagggagt agtaaccttg tttatattgg     2492
caatatatac ttcctccgtt tctaaatatt tgacgctgtt gacttttttaa acatgtttga   2552 ccgttcgtct tattaaaaaa taagtaatta ttaattcttt tcctatcatt tgatttattg    2612
ttaaatatat ttttatgcag acatatagtt ttacatattt cataaaagtt tttgaataag   2672
aagaatgatc gtcaaatatt tagaaacgag gggagtatat tgctagtaaa ttttactgta   2732
aagtcatgtt tcttcatgtg tctttttttag aacatttctt cttcatgtgt tccattcaat  2792
tttttcgatc tccaccacca ctaccacagt tgtatgtgta gtagctagct gttgcacatg   2852
ctcatgttaa tctgaatctg ttcatggttt tttgcag gg caa gag gtg atg tgc     2906
                                        Gly Gln Glu Val Met Cys
                                                105 tac gag agc cca agg cca acc atg ggg atc cac cgg ctg gtg ttc gtg     2954
Tyr Glu Ser Pro Arg Pro Thr Met Gly Ile His Arg Leu Val Phe Val
110             115                 120                 125 ctg ttc cag cag ctg ggg cgt cag aca gtg tac gcg ccc ggg tgg cgt     3002
Leu Phe Gln Gln Leu Gly Arg Gln Thr Val Tyr Ala Pro Gly Trp Arg
        130                 135                 140 cag aac ttc aac acc aag gac ttc gcc gag ctc tac aac ctc ggc tcg     3050
Gln Asn Phe Asn Thr Lys Asp Phe Ala Glu Leu Tyr Asn Leu Gly Ser
145                 150                 155 ccg gtc gcc gcc gtc tac ttc aac tgc cag cgc gag gcc ggc tcc ggc     3098
Pro Val Ala Ala Val Tyr Phe Asn Cys Gln Arg Glu Ala Gly Ser Gly
        160                 165                 170 ggc agg agg gtc tac aac tag ctaacgatga tcccgatcga tctgctgcat        3149
Gly Arg Arg Val Tyr Asn
        175 gctcactatc atcatccagc atgctataca ttgcaggttc agacaattga atgattctc    3209 gacacacaac atatatatga tggtgtaatt aattatgcaa ttaattagct gagcaaggct   3269 aaggtctctc atgaagctag ctttgctcta tatatata tatatatata tatatata      3329 tatatatata tatatatata tatatatata tagtgaagtg tgcaataagc tgcaggtata   3389 taagactgga tttaaggagc taattaacta aaccatgcat cacgtatatg tgagatgcag   3449 tcgtgctctt gcatccaagg atacatacag catatgcatg caatattggt atcatatgca   3509 tgcaatattg gtatcatatg cagcggctgc tagctactcc tagaagctat acagcagaat   3569 gtaaacatat atgtgtagca gtacttatac gtagcacatc gatctgcaca tgttggatgt   3629 agcaagaaat tgctatgaaa tataagtaga gatgtgctta atatcaaatg tgtgtcacat   3689 gtgaatctat cagctgggca tatatagtgt ctctttcagg cttccatctc actgtctatc   3749 tcgccccca ctgaatatat atttcgacag ctgtcgcgtt ccgattcgtc gaaatctctc    3809 gctagcacag tttaaggaca ggtactacgt gctaatgata tgatatgatg gtgaaaggga   3869 ctacagctag ggagtatcaa tcagaaccca tgttttggaa aagctgatac ggatcgtat    3929 tgatcatatg catgcgtaga agaattcatc gtcagaaaac gcgtacgatt ggtcgtatgt   3989 gaaagaagca tatatatcta gatctgtaac tttaaaatcc actctcctat gatcgatcga   4049 gcatccattg gtgagttata tgttcaaaag catagatcga gatcgtcacg attggtagtg   4109
```

-continued

```
ggtgatcgat gcagctatac tagctccttt tctctcccaa tcgtcgaaga ttcaggcatt      4169
cacccaatgc tgttgcaggg atataattgt ctctgttatt ttttattctg acattgtata      4229
```

```
<210> SEQ ID NO 2
<211> LENGTH: 179
<212> TYPE: PRT
<213> ORGANISM: Oryza sativa

<400> SEQUENCE: 2
```

Met Ala Gly Ser Gly Arg Asp Arg Asp Pro Leu Val Val Gly Arg Val
 1               5                  10                  15

Val Gly Asp Val Leu Asp Ala Phe Val Arg Ser Thr Asn Leu Lys Val
                20                  25                  30

Thr Tyr Gly Ser Lys Thr Val Ser Asn Gly Cys Glu Leu Lys Pro Ser
            35                  40                  45

Met Val Thr His Gln Pro Arg Val Glu Val Gly Asn Asp Met Arg
        50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Asn

```
<210> SEQ ID NO 3
<211> LENGTH: 4110
<212> TYPE: DNA
<213> ORGANISM: Oryza sativa
<220> FEATURE:
<223> OTHER INFORMATION: genomic DNA
<220> FEATURE:
<221> NAME/KEY: exon
<222> LOCATION: (812)..(1170)
<220> FEATURE:
<221> NAME/KEY: intron
<222> LOCATION: (1171)..(1332)
<220> FEATURE:
<221> NAME/KEY: exon
<222> LOCATION: (1333)..(1394)
<220> FEATURE:
<221> NAME/KEY: intron
<222> LOCATION: (1395)..(1527)
<220> FEATURE:
<221> NAME/KEY: exon
<222> LOCATION: (1528)..(1568)
<220> FEATURE:
<221> NAME/KEY: intron
<222> LOCATION: (1569)..(2875)
<220> FEATURE:
<221> NAME/KEY: exon
<222> LOCATION: (2876)..(3260)
<220> FEATURE:
<221> NAME/KEY: CDS
<222> LOCATION: (964)..(1170)
```

-continued

```
<220> FEATURE:
<221> NAME/KEY: CDS
<222> LOCATION: (1333)..(1394)
<220> FEATURE:
<221> NAME/KEY: CDS
<222> LOCATION: (1528)..(1568)
<220> FEATURE:
<221> NAME/KEY: CDS
<222> LOCATION: (2876)..(3105)

<400> SEQUENCE: 3
gataagttgc ggaaaaacca acaaattagc aacaaatatg agtaaaactt gtatacatgt      60
gtcttcttag cgatttaaaa atcaatgctg aaaataaatt acaataaaat taaaaatctc     120
aagataatct ctaaaatgta gttttaaaat ttaaattttg attgcgactg ataagaaaaa     180
aaaacaaatg atgggaggct atatcaactg tcaaactggc taatttagaa agacgacatc     240
gaattcctac agattggagg cagcaaaaga gagcccgtct ctgccgggtg cgtgcatgat     300
gctcgatcat atcccatctc tcctcacttc atcatcaaca agaacaagag gaactatata     360
gctgcaagat ctagactgaa actactatag caactaactg tactgtagct agattacgct     420
tagctatagc tgctgctgca tctatctgta aattccaact acgacgtcga ctgctgcaag     480
ctagcttggc cggctagcta gatagctagc tagctcaaaa gagaaagctt tgcgaaatag     540
gagtaactag ctagctctag ctagggcgcc atcgatgcgt gaccaccgag ctcgcctcgt     600
ccacacgtac aggaagacga tgcagaaagc ggccggcatg cagtacactg accgagctaa     660
gagagagaga gagatgatat tattcttctg cagctaaatt aaagtgaaag ttggacatgg     720
acatggacat agtaattttg catggccatc atcttgccct cctatataaa gcggccatct     780
cactctcaac cacagctcga tccagcagcc ctgcaccaca cacagttcag ctagcagatc     840
acctagctag atagctgcct ctatcacagt atatttgctc cctgcaactt gctgctgctg     900
caatagctag cagctgcagc tagtaagcaa aactataaac cttcagggtt ttttgcaaga     960 tcg atg gcc gga agt ggc agg gac agg gac cct ctt gtg gtt ggt agg    1008
    Met Ala Gly Ser Gly Arg Asp Arg Asp Pro Leu Val Val Gly Arg
    1               5                  10                  15 gtt gtg ggt gat gtg ctg gac gcg ttc gtc cgg agc acc aac ctc aag    1056
Val Val Gly Asp Val Leu Asp Ala Phe Val Arg Ser Thr Asn Leu Lys
            20                  25                  30 gtc acc tat ggc tcc aag acc gtg tcc aat ggc tgc gag ctc aag ccg    1104
Val Thr Tyr Gly Ser Lys Thr Val Ser Asn Gly Cys Glu Leu Lys Pro
        35                  40                  45 tcc atg gtc acc cac cag cct agg gtc gag gtc ggc ggc aat gac atg    1152
Ser Met Val Thr His Gln Pro Arg Val Glu Val Gly Gly Asn Asp Met
    50                  55                  60 agg aca ttc tac acc ctt gtatgtgagc tctaccatgt gtcgtagttg            1200
Arg Thr Phe Tyr Thr Leu
65 gtgcagagac cagaagttat actttctttc attattatat tatagaaaaa tttgtttggt   1260 acttaaccca agatgacttt aaaatgcatt aatttgatgt ttgtcatggt tttttgtggt   1320 gtgtacctga ag gtg atg gta gac cca gat gca cca agc cca agt gac cct   1371
              Val Met Val Asp Pro Asp Ala Pro Ser Pro Ser Asp Pro
                 70                  75                  80 aac ctt agg gag tat cta cat tg gtaagcacac taatgttaag ctagcgcact     1424
Asn Leu Arg Glu Tyr Leu His Trp
            85                  90 tgttttcatg caatgatcaa aataatcact gctagctgat ttacatacat aaccacatct   1484
tgactgcatg atgggttgat catcttaatt tgtttgtcca cag g ttg gtc act gat   1540
```

```
                          Leu Val Thr Asp att cct ggt act act gca gcg tca ttt g gtcagtatta aacgatcaaa       1588
Ile Pro Gly Thr Thr Ala Ala Ser Phe
 95                 100 tggtttagat tgatttgatt tcccacttaa atacattgca gtataaaact aacagaggta  1648
aattgtcttt ccatactatt gtttggggg ggggggccag gggcagtga gttgttgagc    1708 attttccctc actcgcgagc ccccagtttg ccgcattaat tccccatcat ccttcaccac  1768
cacaaaaaaa aaagtgattt ggagaaggat acgctcctcc aaataatttt taacaagttc  1828
accaccacaa cgaggcaccg acaaccgcca tgagtccacg caccctgcag ctagtcgtgc  1888
caccagcacc acagttagcc acaccgcgag caatccacgc catcacttgc cgctgtgagt  1948
ccacgatcac acgcctcgat cagccagctg ccatgatatg tcggcttggg cttggattct  2008
gcaacatacc atgtccccat cgatggcacc acactctaat tcgccaacac aacactgaag  2068
ggatcggatc gggagggcta gctcactcaa gatagtgacg ggatgattcg atgggaattc  2128
catggggaac aaagcacaaa atcattaaaa tgtccttttc aattccatgg caaattccta  2188
aagcaatact ctctctccat tctataatgt aggttgcaca ctcatttcaa gattcaactt  2248
tcaaaacatt tgactaacga tttgtataat ataaattgaa ttttatttga tagaaataat  2308
attattggat tgatatttca atatactttc tatggttat aattttgtta ctacaaactt    2368
tatagtatat tagaaattat aaataaaaaa ttagttttgt agaccgtaca tgccaagttt   2428
gaccatacca tattatgaaa agagggagt agtaaccttg tttatatttg caatatatac    2488
tccctccgtt tctaaatatc tgacgctgtt gactttttaa acatgtttga ccgttcgtct   2548
tattaaaaaa taagtaatta ttaattcttt tcctatcatt tgatttattg ttaaatatat   2608
ttttatgcag acatatagtt ttacatattt cataaaagtt tttgaataag aagaatgatc   2668
gtcaaatatt tagaaacgag gggagtatat tgctagtaaa ttttactgta aagtcatgtt   2728
tcttcatgtg tctttttag aacatttctt cttcatgtgt tccaatcaat tttttcgatc    2788
tccaccacca ctaccacagt tgtatgtgta gtagctagct gttgcacatg ctcatgttaa   2848
tctgaatctg tccatggttt tttgcag gg caa gag gtg atg tgc tac gag agc   2901
                                Gly Gln Glu Val Met Cys Tyr Glu Ser
                                                105                 110 cca agg cca acc atg ggg atc cac cgg ctg gtg ttc gtg ctg ttc cag    2949
Pro Arg Pro Thr Met Gly Ile His Arg Leu Val Phe Val Leu Phe Gln
    115                 120                 125 cag ctg ggg cgt cag aca gtg tac gcg ccc ggg tgg cgt cag aac ttc    2997
Gln Leu Gly Arg Gln Thr Val Tyr Ala Pro Gly Trp Arg Gln Asn Phe
130                 135                 140 aac acc aag gac ttc gcc gag ctc tac aac ctc ggc tcg ccg gtc gcc    3045
Asn Thr Lys Asp Phe Ala Glu Leu Tyr Asn Leu Gly Ser Pro Val Ala
145                 150                 155                 160 gcc gtc tac ttc aac tgc cag cgc gag gca ggc tcc ggc ggc agg agg    3093
Ala Val Tyr Phe Asn Cys Gln Arg Glu Ala Gly Ser Gly Gly Arg Arg
                165                 170                 175 gtc tac ccc tag ctaacgatga tcccgatcga tctgctgcat gctcactatc        3145
Val Tyr Pro atcatccagc atgctataca ttgcaggttc agacaattga atgattctc gacacacaac    3205 atatatatga tggtgtaatt aattatgcaa ttaaatagct gagcaaggct aaggtctctc    3265
atgaagctag ctttgctcta tatatatata tatatatata tagtgaagtg tgcaataagc    3325
tgcaagtata taagactgga tttaaggagc taattaacta aaccatgcat catgtatatg   3385
```

```
tgagatgcag tcgtgctctt gcatccaagg atacatacag catatgcatg caatattggt    3445
atcatatgca gcggctgcta gctactccta gatcaagcta tacagcagaa tgtaaacata    3505
tatgtgtagc agtacttata cgtagcacat cgatctgcac atgttggatg tagcaagaaa    3565
ttgctatgaa atataagtag agatgtgctt aatatcaaat gtgtatcaca tgtgaatcta    3625
tcagctgggc atatatagtg tctctttcag gcttccatct cactgtctat ctcgcccccc    3685
actgaatatg cccagtttaa ggacaggtac tacgtgctga tgatatgata tgatggtgaa    3745
agggactaca gctagggagt atcaatcaga acccatgttt tggaaaagct gatacggatc    3805
gatattgatc atatgcatgc gtagaagaat tcatcgtcag aaaacgcgta cgattggtcg    3865
tatgtgaaag aagcatatat atctagatct gtaactttaa aatccactct cctatgatcg    3925
atcgagcatc cattggtgag ttatatgttc aaaagcatcg atcgagatcg tcacgattgg    3985
tagtgggtga tcgatgcagc tatactagct cctttctctc cccaatcgtc gaagattcag    4045
gcattcagcc aatgctgttg cagggatata attgtctctg ttatttttta ttctgacatt    4105
gtata                                                                4110
```

<210> SEQ ID NO 4
<211> LENGTH: 179
<212> TYPE: PRT
<213> ORGANISM: Oryza sativa

<400> SEQUENCE: 4

```
Met Ala Gly Ser Gly Arg Asp Arg Asp Pro Leu Val Val Gly Arg Val
 1               5                  10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
           100                 105                 110

Pro Arg Pro Thr Met Gly Ile His Arg Leu Val Phe Val Leu Phe Gln
       115                  120                 125

Gln Leu Gly Arg Gln Thr Val Tyr Ala Pro Gly Trp Arg Gln Asn Phe
   130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 5
gagtaatttg cggtcagagt c                21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 6
ccaaacaaca catcctcag                19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 7
accgcaggtc tccttgtcat t                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 8
gctattgcca tcgccttgtg t                21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 9
tcagaacttc aacaccaagg                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
accttagcct tgctcagcta                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11
gggagaatat gttgcagtag                                            20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 12
caaatggtaa tgggtcaa                                              18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13
ctgtctcgaa atcgcctctg                                            20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 14
tccagcacat cacccacaa                                             19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 15
agcctctgcg tcactgtcat c                                          21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 16
gcagcagcaa actcccaaag                                            20

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 17
ggggacgtcg gacctgt                                               17

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 18
agttgaagtt tgggctggtc g                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 19
tccatcttgg catctctcag                                                20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 20
gtacccgcat caggcatctg                                                20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 21
gctgcctcta tcacagtata tt                                             22

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 22
cgctcagcaa cgagtttc                                                  18

<210> SEQ ID NO 23
<211> LENGTH: 847
<212> TYPE: DNA
<213> ORGANISM: Oryza sativa

<400> SEQUENCE: 23
tgcaccacac acagttcagc tagcagatca cctagctaga tagctgcctc tatcacagta     60
tatttgctcc ctgcaacttg ctgctgctgc aatagctagc agctgcagct agtaagcaaa    120
actatatacc ttcagggttt tttgcaagat cgatggccgg aagtggcagg gacagggacc    180

```
ctcttgtggt tggtagggtt gtgggtgatg tgctggacgc gttcgtccgg agcaccaacc      240
tcaaggtcac ctatggctcc aagaccgtgt ccaatggctg cgagctcaag ccgtccatgg      300
tcacccacca gcctagggtc gaggtcggcg gcaatgacat gaggacattc tacacccttg      360
tgatggtaga cccagatgca ccaagcccaa gtgaccctaa ccttagggag tatctacatt      420
ggttggtcac tgatattcct ggtactactg cagcgtcatt tgggcaagag gtgatgtgct      480
acgagagccc aaggccaacc atggggatcc accggctggt gttcgtgctg ttccagcagc      540
tggggcgtca gacagtgtac gcgcccgggt ggcgtcagaa cttcaacacc aaggacttcg      600
ccgagctcta caacctcggc tcgccggtcg ccgccgtcta cttcaactgc cagcgcgagg      660
ccggctccgg cggcaggagg gtctacaact agctaacgat gatcccgatc gatctgctgc      720
atgctcacta tcatcatcca gcatgctata cattgcaggt tcagacaatt gaaatgattc      780
tcgacacaca acatatatat gatggtgtaa ttaattatgc aattaattag ctgagcaagg      840
ctaaggt                                                                847

<210> SEQ ID NO 24
<211> LENGTH: 847
<212> TYPE: DNA
<213> ORGANISM: Oryza sativa

<400> SEQUENCE: 24
tgcaccacac acagttcagc tagcagatca cctagctaga tagctgcctc tatcacagta       60
tatttgctcc ctgcaacttg ctgctgctgc aatagctagc agctgcagct agtaagcaaa      120
actataaacc ttcagggttt tttgcaagat cgatggccgg aagtggcagg gacagggacc      180
ctcttgtggt tggtagggtt gtgggtgatg tgctggacgc gttcgtccgg agcaccaacc      240
tcaaggtcac ctatggctcc aagaccgtgt ccaatggctg cgagctcaag ccgtccatgg      300
tcacccacca gcctagggtc gaggtcggcg gcaatgacat gaggacattc tacacccttg      360
tgatggtaga cccagatgca ccaagcccaa gtgaccctaa ccttagggag tatctacatt      420
ggttggtcac tgatattcct ggtactactg cagcgtcatt tgggcaagag gtgatgtgct      480
acgagagccc aaggccaacc atggggatcc accggctggt gttcgtgctg ttccagcagc      540
tggggcgtca gacagtgtac gcgcccgggt ggcgtcagaa cttcaacacc aaggacttcg      600
ccgagctcta caacctcggc tcgccggtcg ccgccgtcta cttcaactgc cagcgcgagg      660
caggctccgg cggcaggagg gtctaccct agctaacgat gatcccgatc gatctgctgc       720
atgctcacta tcatcatcca gcatgctata cattgcaggt tcagacaatt gaaatgattc      780
tcgacacaca acatatatat gatggtgtaa ttaattatgc aattaaatag ctgagcaagg      840
ctaaggt                                                                847
```

HD3A GENE INDUCING FLOWERING OF PLANT AND UTILIZATION THEREOF

TECHNICAL FIELD

The present invention relates to genes that induce flowering in plants, and methods for modifying the flowering time of plants using the genes. The methods for modifying the flowering time of plants are useful for plant breeding and such.

BACKGROUND ART

Generally, heading (flowering) of rice is promoted by short-day conditions and delayed by long-day conditions. Among known cultivars, typically those from Kyushu and the south of Mainland Japan have strong photoperiod sensitivity whereas cultivars from the Tohoku district or Hokkaido show complete loss of such sensitivity or have extremely weak photoperiod sensitivity. Rice plants that lack the photoperiod sensitivity have a characteristic to flower after a certain length of growth period, and the heading date of the plant does not change with changes in photoperiod. Adaptation of rice plants in particular locations and seasons drastically changes in accordance with the existence of photoperiod sensitivity in the plant. Thus, modification of photoperiod sensitivity in rice is an important aspect of rice breeding.

In conventional breeding programs, the alteration of the heading date of rice is achieved through methods involving: (1) selection of early maturing varieties or late varieties by crossing; and (2) mutagenesis by radiation and chemicals; and so on. However, such breeding programs require long periods of time to be successful, and bear other problems, such as unpredictability of the degree or direction of the variation in the progeny.

The term "photoperiod sensitivity gene" is a generic term for genes that enhance the rice photoperiod sensitivity in the field of rice genetics. The existence of several photoperiod sensitivity genes has been observed to be inherent in mutants and cultivars, and photoperiod sensitivity genes are suggested to exist on loci, for example, such as Sel locus (chromosome 6; Yokoo and Fujimaki (1971) Japan. J. Breed. 21:35–39), E1 locus (chromosome 7; Tsai, K. H. (1976) Jpn. J. Genet. 51: 115–128; Okumoto, Y. et al. (1992) Jpn. J. Breed. 42: 415–429), E2 locus (unknown), E3 locus (chromosome 3; Okumoto et al. Japanese Society of Breeding, 91st lecture, Japanese Journal of Breeding 47(Suppl. 1): 31), and so on (Yamagata et al. (1986) In Rice Genetics, International Rice Research Institute, Manilla, pp351–359).

When a photoperiod sensitivity gene of rice or a gene regulating the heading of rice under the control of the photoperiod sensitivity gene is isolated, introduction of the gene into any desired rice cultivar by a transformation method makes it possible to control the heading time of the rice cultivar. Furthermore, the flowering time of various plants can be controlled by utilizing genes of other plants corresponding to such rice photoperiod sensitivity gene. This kind of breeding method can be said to be extremely advantageous compared to conventional methods in the aspect of convenience and reliability.

DISCLOSURE OF THE INVENTION

The present invention was made in view of these circumstances. An object of the present invention is to provide novel genes controlling the flowering of a plant. Furthermore, another object of the present invention is to modify the flowering time of a plant using such genes.

The present inventors particularly focused on rice among plants, for which the development of a convenient method for modifying the heading time (flowing time) is strongly desired, and actively pursued the isolation of genes associated with the heading of rice.

In rice, Hd3a, a quantitative trait loci (QTL), detected by using progenies derived from a cross between Nipponbare and Kasalath, had been revealed to be located on the short arm of chromosome 6. Furthermore, the analysis using a nearly isogenic line of Hd3a region (allele of Kasalath) having the genetic background of Nipponbare revealed that the Hd3a locus is identical to a photoperiod sensitivity gene locus promoting heading under short-day condition.

To isolate the photoperiod sensitivity gene Hd3a, which had been known to exist but had not yet been identified, the present inventors first mapped the Hd3a gene region by linkage analysis with P1-derived artificial chromosome (PAC) clones. Specifically, detailed linkage analysis of the Hd3a region was performed with a large segregating population essential for map base cloning. First, using the segregating population of the Hd3a region, a linkage map was constructed using restriction fragment length polymorphism (RFLP) markers and it was proved that Hd3a was located in the interval between RELP markers C764 and B174 (Monna, et al., the 1999 Annual Meeting of Japanese Society of Molecular Biology). Furthermore, utilizing cleaved amplified polymorphic sequence (CAPS) markers CP13 and CP15 flanking both sides of Hd3a, plants having chromosomes with a recombination occurred in the vicinity of Hd3a were selected from a population having the Hd3a region segregated to determine their genotype by the progeny assay. Eight (8) individuals having recombination between the Hd3a and CP13 were identified, two (2) between Hd3a and CP15.

Next, the present inventors conducted alignment of the Hd3a gene region using P1-derived artificial chromosome (PAC) clones. Specifically, 3 types of PAC clones having sequences of DNA markers existing in the vicinity of the Hd3a locus were screened from the Nipponbare PAC genomic library. P0046E09 and P0698G05 clones had the nucleotide sequences of markers, CP13 and CP15, which are flanking both sides of Hd3a, and thus these PAC clones were revealed to comprise the Hd3a gene region (FIG. 1). As a result of nucleotide sequence analysis of the PAC clone P0046E09, the candidate genomic region was limited within a region of about 20 kb. Gene prediction and homology search against the nucleotide sequence of this candidate region detected regions showing high homology to the lipid transfer protein, acyl-CoA synthase genes, and FT gene of *Arabidopsis*.

Then, the expression of these candidate genes was analyzed by RT-PCR using Nipponbare and a nearly isogenic line (NIL (Hd3a)) wherein the Hd3a gene region had been substituted with Kasalath chromosome segment. As a result, expression of all the three genes was confirmed, and increase in the transcription level of the FT-like gene was observed under short-day condition (FIG. 2). Thus, the FT-like gene was selected as the potential Hd3a candidate gene.

A cosmid library was constructed from the genomic DNA of Kasalath. A clone corresponding to the FT-like gene region was screened from the cosmid library (FIG. 1), and the nucleotide sequence of the FT-like gene region was analyzed. As a result, mutations at 41 sites (insertion, deletion, and substitution of nucleotides) were found in that of Kasalath as compared to the nucleotide sequence of Nipponbare (FIG. 3). A nucleotide substitution within the exon caused an amino acid substitution of asparagine (Kasalath) to proline (Nipponbare) (FIG. 3).

Next, the present inventors introduced a fragment containing only the candidate gene region of Kasalath or Nipponbare into a transformable vector to transform rice plants, and analyzed the phenotype of the resulting transformant. As a result, among the plants having these genes introduced appeared plants that showed early heading under both short-day and long-day conditions. However, significant changes in the heading time were not observed among plants introduced with the vector alone (Table 1). Furthermore, self-pollinated progenies from the transformed plants that showed early-heading under short-day condition were cultivated to examine the difference in the number of days from sowing to heading (days to heading). As a result, plants showing early heading time compared to the control were segregated, and all the plants showing early heading contained the introduced gene (FIG. 4A). Similarly, under long-day conditions, in contrast to the control that did not reach the heading stage, heading plants was observed among the above-described self-pollinated progenies, and all of such plants retained the introduced fragment (FIG. 4B).

The above-described results confirmed that the candidate FT-like gene has the function to promote the heading (flowering) of rice, and it was concluded that the candidate FT-like gene is Hd3a gene. The Hd3a gene is widely distributed in plants and is suggested to be associated with the induction of flowering of these plants.

Finally, the present inventors succeeded in isolating the Hd3a gene that induces flowering of plant. The present inventors also found that the flowering time of plants can be modified using the gene, and completed the present invention.

More specifically, this invention provides the following:

(1) a DNA encoding a protein derived from plants which induces the flowering of plants, wherein said DNA is selected from the group consisting of:

(a) a DNA encoding the protein comprising the amino acid sequence of SEQ ID NO: 2 or 4;

(b) a DNA encoding the protein comprising the amino acid sequence of SEQ ID NO: 2 or 4, wherein one or more of the amino acids are substituted, deleted, added, and/or inserted; and (c) a DNA hybridizing under stringent conditions with the DNA consisting of the nucleotide sequence of any one of SEQ ID NO: 1, 3, 23 or 24;

(2) the DNA of (1), wherein the DNA is derived from rice;

(3) a DNA encoding an antisense RNA complementary to the transcription product of the DNA of (1) or (2);

(4) a DNA encoding an RNA having the activity of a ribozyme that specifically digests the transcription product of the DNA of (1) or (2);

(5) a DNA encoding an RNA that represses the expression of the DNA of (1) or (2) upon expression in a plant cell due to a co-repressing effect;

(6) a DNA of (1) or (2), wherein the DNA is used to induce the flowering of plant;

(7) a DNA of any one of (3) to (5), wherein the DNA is used to suppress the flowering of plant;

(8) a vector comprising the DNA of any one of (1) to (5);

(9) a plant cell introduced with the vector of (8);

(10) a plant transformant comprising the plant cell of (9);

(11) the plant transformant of (10), wherein said plant transformant is rice;

(12) a plant transformant which is a progeny or a clone of the plant transformant of (10) or (11);

(13) a breeding material of the plant transformant of any one of (10) to (12);

(14) a method for producing a plant transformant of (10) or (11), which comprises the following steps of:

(a) introducing the DNA of (1) or (2) into a plant cell, and (b) regenerating a plant from the plant cell;

(15) a method for inducing the flowering of plant, wherein said method comprises the step of expressing the DNA of (1) or (2) in cells of the plant body;

(16) a method for suppressing the flowering of plant, which is characterized by the repression of the expression of endogenous DNA of (1) or (2) in cells of the plant body;

(17) the method of (16), which comprises the step of expressing the DNA of any one of (3) to (5) in cells of the plant body; and

(18) the method of any one of (14) to (17), wherein the plant is rice.

The present invention provides DNA encoding the Hd3a protein. The nucleotide sequences of Hd3a genomic DNA and cDNA of Kasalath are set forth in SEQ ID NO: 1 and SEQ ID NO: 23, respectively, and the amino acid sequence of protein encoded by these DNAs in SEQ ID NO: 2. Furthermore, the nucleotide sequences of Hd3a genomic DNA and cDNA of Nipponbare are set forth in SEQ ID NO: 0.3 and SEQ ID NO: 24, respectively, and the amino acid sequence of protein encoded by these DNAs in SEQ ID NO: 4.

Hd3a is one of quantitative trait loci (QTL) that was detected using the progeny derived from a cross between Nipponbare and Kasalath, and was proved to be located on the short arm of chromosome 6. Furthermore, analysis of the nearly isogenic line of the Kasalath allele of Hd3a with the genetic background of Nipponbare revealed that the Hd3a locus promotes heading under short-day condition.

Although Hd3a is known to be a gene having the action to promote heading under short-day condition existing anywhere within a broad region of the short arm of rice chromosome 6, the gene itself has not yet been identified or isolated. The present inventors have finally elucidated the existing region of Hd3a through complicated steps, succeeding for the first time in isolating the Hd3a gene as a single gene.

Currently, the control of heading time is an important target in the breeding of rice cultivars in Japan. In cold districts, due to the early arrival of autumn and low temperatures, the control of heading time is critical to avoid cold-weather damage. On the other hand, in southwest warm regions, to avoid concentrated harvesting labor in large scale rice growing zones, fine modification of heading date of rice is required.

Hd3a has the function to induce flowering. Therefore, the use of the sense strand of Hd3a gene for transformation enables the promotion of the heading in rice (flowering). On the other hand, the introduction of the gene in the antisense direction enables the suppression of flowering. The time needed for such transformation techniques in plant breeding is remarkably short as compared to gene transfer by cross breeding. Furthermore, the fact that the transformation does not accompany other changes of the trait is also beneficial. Accordingly, the flowering time of a plant can be readily altered using the isolated Hd3a gene. Therefore, the gene contributes to the breeding of rice cultivars particularly adapted to different districts. Furthermore, the heading time of plants can be diversified and novel plant cultivars may be bred for cultivars that are deficient in the Hd3a gene by introducing the gene by genetic recombination, and for cultivars having the gene, by controlling the expression of the gene using antisense DNA or ribozymes.

DNAs encoding an Hd3a protein of the present invention include genomic DNAs, cDNAs, and chemically synthesized DNAs. A genomic DNA and cDNA can be prepared according to conventional methods known to those skilled in the art. More specifically, a genomic DNA can be prepared, for example, as follows: (1) extract genomic DNA from rice cultivars having an Hd3a gene (e.g. Kasalath or Nipponbare); (2) construct a genomic library (utilizing a vector, such as plasmid, phage, cosmid, BAC, PAC, and so on); (3) spread the library; and (4) conduct colony hybridization or plaque hybridization using a probe prepared based on the DNA encoding a protein of the present invention 30. (e.g. SEQ ID NO: 1, 3, 23, or 24). Alternatively, a genomic DNA can be prepared by PCR, using primers specific to a DNA encoding a protein of the present invention (e.g. SEQ ID NO: 1, 3, 23, or 24). On the other hand, cDNA can be prepared, for example, as follows: (1) synthesize cDNAs based on mRNAs extracted, from rice cultivars having an Hd3a gene (e.g. Kasalath or Nipponbare); (2) prepare a cDNA library by inserting the synthesized cDNA into vectors, such as λZAP; (3) spread the cDNA library; and (4) conduct colony hybridization or plaque hybridization as described above. Alternatively, cDNA can be also prepared by PCR.

The present invention includes DNAs encoding proteins functionally equivalent to the Hd3a protein of SEQ ID NO: 2 or 4 (Kasalath or Nipponbare). Herein, the term "functionally equivalent to the Hd3a protein" indicates that the object protein has the function of introducing the flowering of plant. Such DNAs are derived preferably from monocotyledonous plants, more preferably from Gramineae, and most preferably from rice.

Examples of such DNAs include those encoding mutants, derivatives, alleles, variants, and homologues comprising the amino acid sequence of SEQ ID NO: 2 or 4 wherein one or more amino acids are substituted, deleted, added and/or inserted.

Examples of methods for preparing a DNA encoding a, protein comprising altered amino acids well known to those skilled in the art include the site-directed mutagenesis (Kramer, W. and Fritz, H. -J., (1987) "Oligonucleotide-directed construction of mutagenesis via gapped duplex DNA." Methods in Enzymology, 154: 350–367); The amino acid sequence of a protein may also be mutated in nature due to the mutation of a nucleotide sequence. A DNA encoding proteins having the amino acid sequence of a natural Hd3a protein wherein one or more amino acids are substituted, deleted, and/or added are also included in the DNA of the present invention, so long as they encode a protein functionally equivalent to a natural Hd3a protein (SEQ ID NO: 2 or 4). Additionally, nucleotide sequence mutants that do not give rise to amino acid sequence changes in the protein (degeneracy mutants) are also included in the DNA of the present invention.

Whether a DNA encodes a protein that induces flowering of a plant or not can be assessed by, for example, as follows: cultivate the plant introduced with a test DNA in a growth chamber wherein the photoperiod can be modified; and examine the number of days required from sowing to flowering (from sowing to heading in rice). Under any photoperiod conditions, a protein is considered to have the flowering promoting-function when it promotes the flowering of a plant compared to a control plant. The flowering promoting-function can be particularly readily proven under a photoperiod condition wherein the flowering of the control plant is suppressed, for example, under long-day conditions (14 to 16 h) for rice, due to the expected widened difference in the flowering time with the comparative control.

A DNA encoding a protein functionally equivalent to an Hd3a protein described in SEQ ID NO: 2 or 4 can be produced, for example, by methods well known to those skilled in the art including: hybridization techniques (Southern, E. M. (1975) Journal of Molecular Biology 98: 503.); and polymerase chain reaction (PCR) techniques (Saiki, R. K. et al. (1985) Science 230: 1350–1354; Saiki, R. K. et al. (1988) Science 239: 487–491). That is, it is routine for a person skilled in the art to isolate a DNA with high homology to the Hd3a gene from rice and other plants using the nucleotide sequence of an Hd3a gene (SEQ ID NO: 1, 3, 23, or 24) or parts thereof as a probe, and oligonucleotides hybridizing specifically to the nucleotide sequence of the Hd3a gene (SEQ ID NO: 1, 3, 23, or 24) as a primer. Such DNA encoding proteins functionally equivalent to an Hd3a protein, obtainable by hybridization techniques or PCR techniques, are included in the DNA of this invention.

Hybridization reactions to isolate such DNAs are preferably conducted under stringent conditions. Stringent hybridization conditions of the present invention include conditions such as: 6 Murea, 0.4% SDS, and 0.5×SSC; and those which yield a similar stringency to the conditions. DNAs with higher homology are expected when hybridization is performed under conditions with higher stringency, for example, 6 M urea, 0.4% SDS, and 0.1×SSC. Those DNAs isolated under such conditions are expected to encode a protein having a high amino acid level homology with an Hd3a protein (SEQ ID NO: 2 or 4). Herein, high homology means an identity of at least 50% or more, more preferably 70% or more, and much more preferably 90% or more (e.g. 95% or more), through the entire amino acid sequence.

The degree of homology of one amino acid sequence or nucleotide sequence to another can be determined by following the algorithm BLAST by Karlin and Altschul (Proc. Nati. Acad. Sci. USA 90: 5873–5877, 1993). Programs such as BLASTN and BLASTX developed based on this algorithm (Altschul et al. (1990) J. Mol. Biol. 215: 403–410) may be used. To analyze a nucleotide sequence according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST program. Specific techniques for such analysis are known in the art.

For example, plant transformants with modified the flowering time can be created using a DNA of the present invention. More specifically, a DNA encoding a protein of the present invention is inserted into an appropriate vector; the vector is introduced into a plant cell; and then, the resulting transformed plant cell is regenerated. The Hd3a gene isolated by the present inventors functions to induce the flowering. Therefore, the flowering time of arbitrary cultivars can be controlled by transforming the cultivars with the gene and expressing the same. The time needed for transformation is remarkably short as compared to ordinary gene transfer by crossing. Furthermore, the fact that the transformation does not accompany other changes of the trait is also beneficial.

On the other hand, a plant transformant with repressed flowering can be created using DNA that represses the expression of a DNA encoding a protein of the present invention: wherein the DNA is inserted into an appropriate vector, the vector is introduced into a plant cell, and then, the resulting transformed plant cell is regenerated. The phrase "repression of expression of DNA encoding a protein of the present invention" includes repression of gene transcription as well as repression of translation to protein. It also includes not only the complete suppression of DNA expression but also a reduction in expression.

The expression of a specific endogenous gene in plants can be repressed using antisense technology methods, which are commonly used in the art. Ecker et al. were the first to demonstrate the antisense effect of an antisense RNA introduced by electroporation in plant cells using the transient gene expression method (J. R. Ecker and R. W. Davis (1986) Proc. Natl. Acad. Sci. USA 83: 5372). Thereafter, the target gene expression was reportedly reduced in tobacco and petunias by expressing antisense RNAs (A. R. van der Krol et al. (1988) Nature 333: 866). The antisense technique has now been established as a means to repress target gene expression in plants.

Multiple factors cause repression of the target gene expression by antisense nucleic acid. These include: inhibition of transcription initiation resulting from triple strand formation; repression of transcription resulting from hybrids formed at the site where the RNA polymerase has formed a local open loop structure; transcription inhibition resulting from hybrid formation with the RNA being synthesized; repression of splicing resulting from hybrid formation at the junction between an intron and an exon; repression of splicing resulting from hybrid formation at the site of spliceosome formation; repression of mRNA translocation from the nucleus to the cytoplasm resulting from hybrid formation with mRNA; repression of splicing resulting from hybrid formation at the capping site or at the poly A addition site; repression of translation initiation resulting from hybrid formation at the binding site for the translation initiation factors; repression of translation resulting from hybrid formation at the site for ribosome binding near the initiation codon; inhibition of peptide chain elongation resulting from hybrid formation in the translated region or at the polysome binding sites of mRNA; and repression of gene expression resulting from hybrid formation at the sites of interaction between nucleic acids and proteins. These factors repress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society), Tokyo Kagaku Dozin, pp. 319–347, (1993)).

Accordingly, an antisense sequence of the present invention can repress the target gene expression by any of the above mechanisms. In one embodiment, if an antisense sequence is designed to be complementary to the untranslated region near the 5' end of the gene's mRNA, it will effectively inhibit translation of a gene. It is also possible to use sequences complementary to the coding regions or to the untranslated region on the 3' side. Thus, the antisense DNA used in the present invention includes DNA having antisense sequences against both the untranslated regions and the translated regions of the gene. The antisense DNA to be used is connected downstream of an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene of the plant to be transformed or a part thereof, but it need not be perfectly complementary, so long as it can effectively inhibit the gene expression. The transcribed RNA is preferably at least 90%, and more preferably at least 95% complementary to the transcribed products of the target gene. In order to effectively inhibit the expression of the target gene by means of an antisense sequence, the antisense DNA should be at least 15 nucleotides long, more preferably at least 100 nucleotides long, and still more preferably at least 500 nucleotides long. However, the antisense DNA to be used is generally shorter than 5 kb, and preferably shorter than 2.5 kb.

DNAs encoding ribozymes can also be used to repress the expression of endogenous genes. A ribozyme is an RNA molecule that has catalytic activities. There are many ribozymes having various activities. Research on ribozymes as RNA cleaving enzymes has enabled the design of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka (1990) Tanpakushitsu Kakusan Kohso (Nucleic acid, Protein, and Enzyme) 35: 2191).

The self-cleavage domain of a hammerhead type ribozyme cleaves at the 3' side of C15 of the sequence G13U14C15. Formation of a nucleotide pair between U14 and A at the ninth position is considered to be important for the ribozyme activity. Furthermore, it has been shown that the cleavage also occurs when the nucleotide at the 15th position is A or U instead of C (M. Koizumi et al. (1988) FEBS Lett. 228: 225) If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (M. Koizumi et al. (1988) FEBS Lett. 239: 285; Makoto Koizumi and Eiko Ohtsuka (1990) Tanpakushitsu Kakusan Kohso (Protein, Nucleic acid, and Enzyme) 35: 2191; M. Koizumi et al. (1989) Nucleic Acids Res. 17: 7059). For example, in the coding region of the Hd3a gene (SEQ ID NO: 1, 3, 23, or 24), there are a plurality of sites that can be used as ribozyme targets.

The hairpin type ribozyme is also useful in the present invention. A hairpin type ribozyme can be found, for example, in the minus strand of the satellite RNA of tobacco ringspot virus (J. M. Buzayan (1986) Nature 323: 349). This ribozyme has also been shown to target-specifically cleave RNA (Y. Kikuchi and N. Sasaki (1992) Nucleic Acids Res. 19: 6751; Yo Kikuchi (1992) Kagaku To Seibutsu (Chemistry and Biology) 30: 112).

The ribozyme designed to cleave the target is fused with a promoter, such as the cauliflower mosaic virus 35S promoter, and with a transcription termination sequence, so that it will be transcribed in plant cells. However, if extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (K. Taira et al. (1990) Protein Eng. 3: 733; A. M. Dzaianott and J. J. Bujarski (1989) Proc. Natl. Acad. Sci. USA 86: 4823; C. A. Grosshands and R. T. Cech (1991) Nucleic Acids Res. 19: 3875; K. Taira et al. (1991) Nucleic Acid Res. 19: 5125). Multiple sites within the target gene can be cleaved by arranging these structural units in tandem to achieve greater effects (N. Yuyama et al. Biochem.

Biophys. Res. Commun. 186: 1271 (1992)). Using such ribozymes, it is possible to specifically cleave the transcription products of the target gene in the present invention, thereby repressing the expression of the gene.

Endogenous gene expression can also be repressed by co-repression, through transformation with a DNA having a sequence identical or similar to the target gene sequence. "Co-repression" refers to the phenomenon wherein, when a gene having a sequence identical or similar to the target endogenous gene sequence is introduced into plants by transformation, expression of both the introduced exogenous gene and the target endogenous gene becomes repressed. Although the detailed mechanism of co-repression is unknown, it is frequently observed in plants (Curr. Biol. 7: R793, 1997; Curr. Biol. 6: 810, 1996). For example, if one wishes to obtain a plant body in which the Hd3a gene is co-repressed, the plant in question can be transformed with a vector DNA designed to express the Hd3a gene or DNA having a similar sequence to select a plant with suppressed the flowering compared to wild-type plant, among the resultant plants. The gene to be used for co-repression does not need to be completely identical to the target gene, but it should have at least 70% or more sequence identity, preferably 80% or more sequence identity, and more preferably 90% or more (e.g. 95% or more) sequence identity. Sequence identity may be determined by the above-described method.

In addition, endogenous gene expression in the present invention can also be repressed by transforming the plant with a gene having the dominant negative phenotype of the target gene. A gene having the dominant negative phenotype refers to a gene which, when expressed, can eliminate or reduce the activity of the wild type endogenous gene inherent to the plant.

Vectors used for the transformation of plant cells are not limited so long as the vector can express inserted genes in plant cells. For example, vectors comprising promoters for constitutive gene expression in plant cells (e.g., cauliflower mosaic virus 35S promoter); and promoters inducible by exogenous stimuli can be used. The term "plant cell" used herein includes various forms of plant cells, such as cultured cell suspensions, protoplasts, leaf sections, and callus.

A vector can be introduced into plant cells by known methods, such as the polyethylene glycol method, electroporation, Agrobacterium mediated transfer; and particle bombardment. Plants can be regenerated from transformed plant cells by known methods depending on the type of the plant cell (see Toki et al., (1995) Plant Physiol. 100:1503–1507).

For example, transformation and regeneration methods for rice plants include: (1) introducing genes into protoplasts using polyethylene glycol, and regenerating the plant body (suitable for indica rice cultivars) (Datta, S. K. (1995) in "Gene Transfer To Plants", Potrykus I and Spangenberg Eds., pp 66–74); (2) introducing genes into protoplasts using electric pulse, and regenerating the plant body (suitable for japonica rice cultivars) (Tokietal. (1992) Plant Physiol. 100: 1503–1507); (3) introducing genes directly into cells by the particle bombardment, and regenerating the plant body (Christou et al. (1991) Bio/Technology, 9: 957–962); (4) introducing genes using Agrobacterium, and regenerating the plant body (Hiei et al. (1994) Plant J. 6: 271–282); and so on. These methods are already established in the art and are widely used in the technical field of the present invention. Such methods can be suitably used for the present invention.

Once a transformed plant, wherein a DNA of the present invention is introduced into the genome, is obtained, it is possible to gain descendants from that plant body by sexual or vegetative propagation. Alternatively, plants can be mass-produced from breeding materials (for example, seeds, fruits, ears, tubers, tubercles, tubs, callus, protoplast, etc.) obtained from the plant, as well as descendants or clones thereof. Plant cells transformed with a DNA of the present invention, plant bodies including these cells, descendants and clones of the plant, as well as breeding materials obtained from the plant, its descendant and clones, are all included in the present invention.

The resulting plant prepared as above is different from that of wild-type plants in terms of the flowering time. For example, plants into which a DNA encoding an Hd3a protein is introduced have decreased time to flowering under paddy field conditions. On the other hand, plants wherein the expression of a DNA encoding an Hd3a protein is repressed due to the introduction of antisense DNAs, have delayed flowering time. Thus, the time needed for flowering of plants can be regulated by controlling the expression of the Hd3a gene. According to the present invention, the heading date of rice, a valuable crop, can be readily controlled, which is extremely beneficial in the breeding of rice cultivars adapted to a particular environment.

A: a linkage map prepared using segregating populations of 2207 plants;

B: Nipponbare-derived PAC clones located in the Hd3a region;

C: an enlarged map of the vicinity of the Hd3a region. Black closed circles on the line represent CAPS markers; arrows indicate the predicted gene regions; and Rec. shows the approximate recombination positions of recombinant individuals. The candidate region is represented by a square. DNA fragments used in the transformation are also shown in the lower part of the map.

Figure 2:
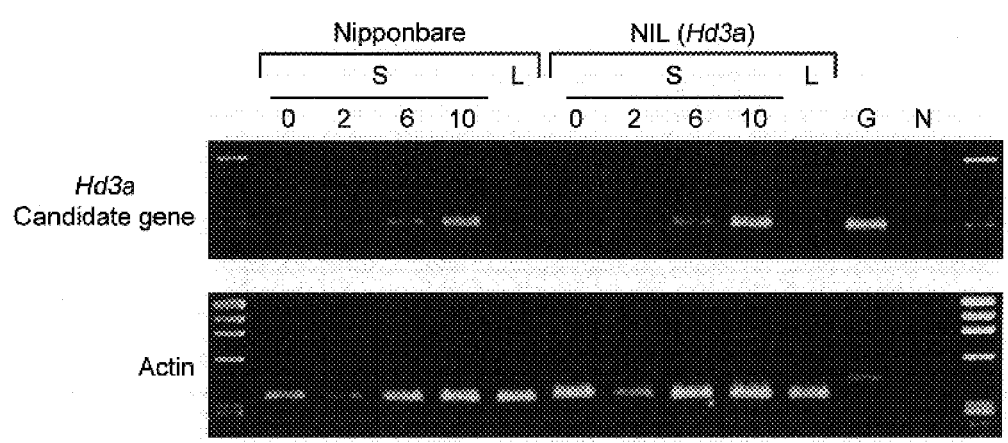

FIG. 2 depicts photographs showing changes in the amount of transcripts of the FT-like gene in rice cultivated under different photoperiod conditions. "S" represents transcripts in plants that have been cultivated under long-day condition (16 h daylight) for 30 days after sowing, then shifted to short-day treatment (10h daylight) and cultivated for 0, 2, 6, and 10 days. "L" represents transcripts from plants that have been further cultivated for 10 days under the long-day condition. "G" represents the genomic DNA; and "N" the control transcript obtained without the template.

Figure 3:
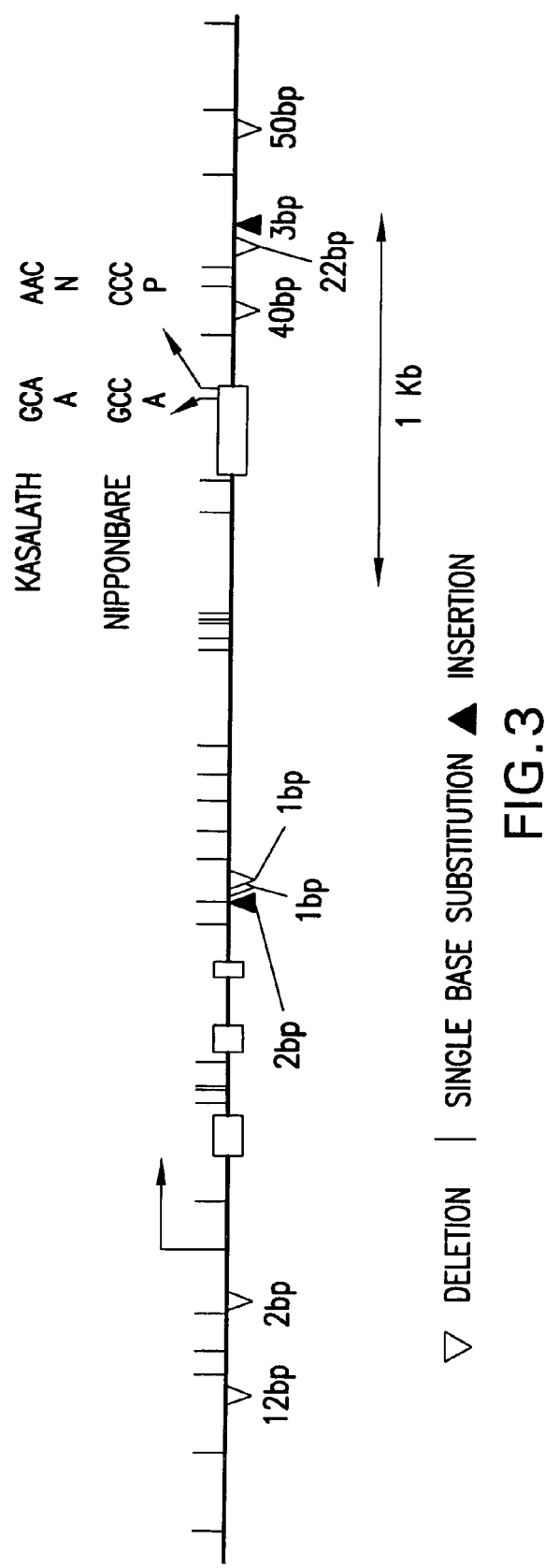

FIG. 3 depicts a diagram showing the Hd3a gene structure. Boxes represent the translation region. Positions of Nipponbare with different sequence to Kasalath are shown in the figure. The transcription initiation site is indicated by the arrow pointing left in the figure.

Figure 4A:
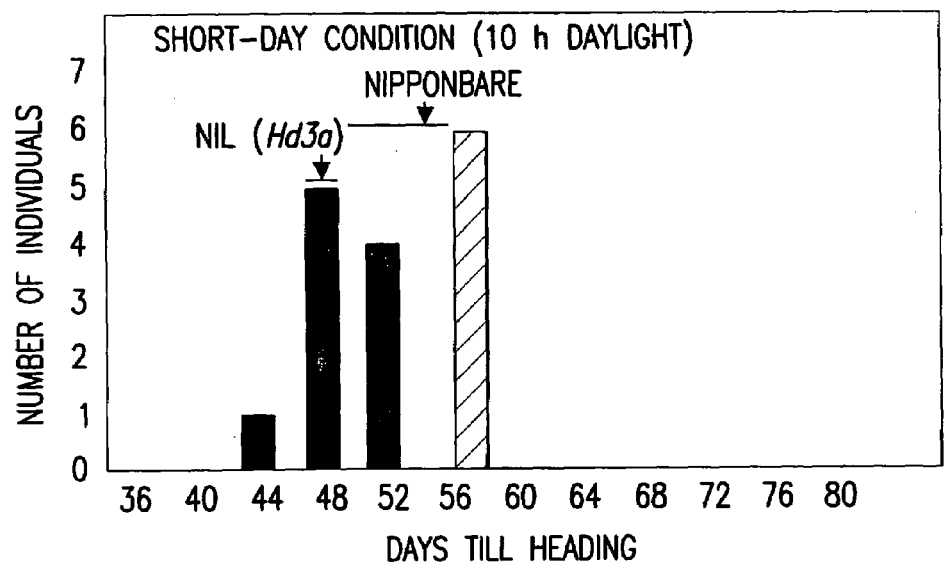
Figure 4B:
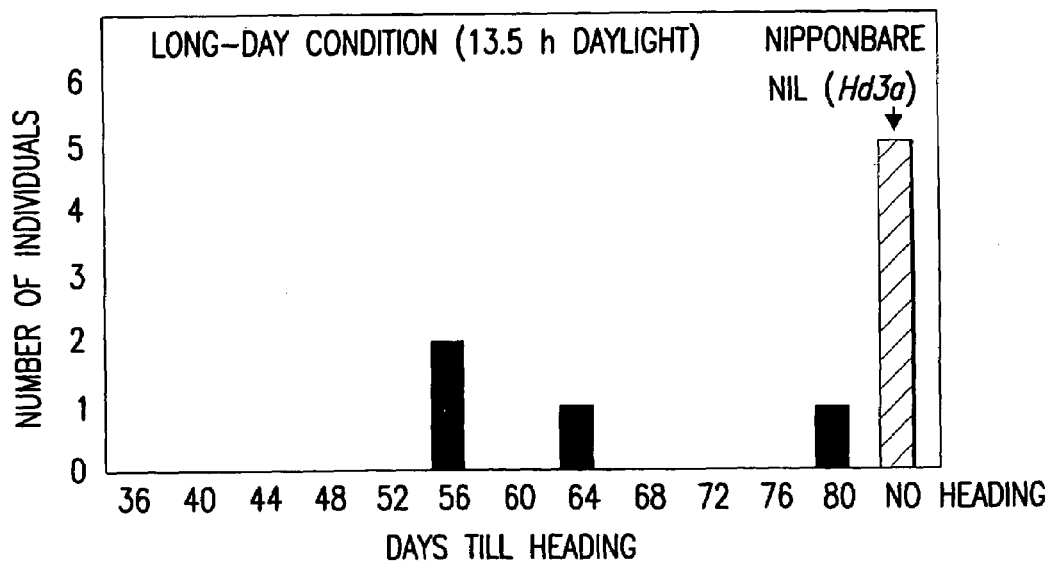

FIGS. 4A and 4B depict bar graphs showing the frequency distribution of number of days to heading in the self-pollinated progenies (T1) of transformed rice plants under the short-day (FIG. 4A) and long-day (FIG. 4B) conditions, respectively. In both figures, dark bars represent plants having the transgene, and bars with slanted lines those without the transgene. Under the long-day conditions, no heading was observed in either Nipponbare or NIL (Hd3a), even after 100 days.

BEST MODE FOR CARRYING OUT THE INVENTION

Herein below, the present invention is specifically described with reference to Examples; however, it is not to be construed as being limited thereto.

EXAMPLE 1

High-resolution Linkage Analysis

Figure 1:
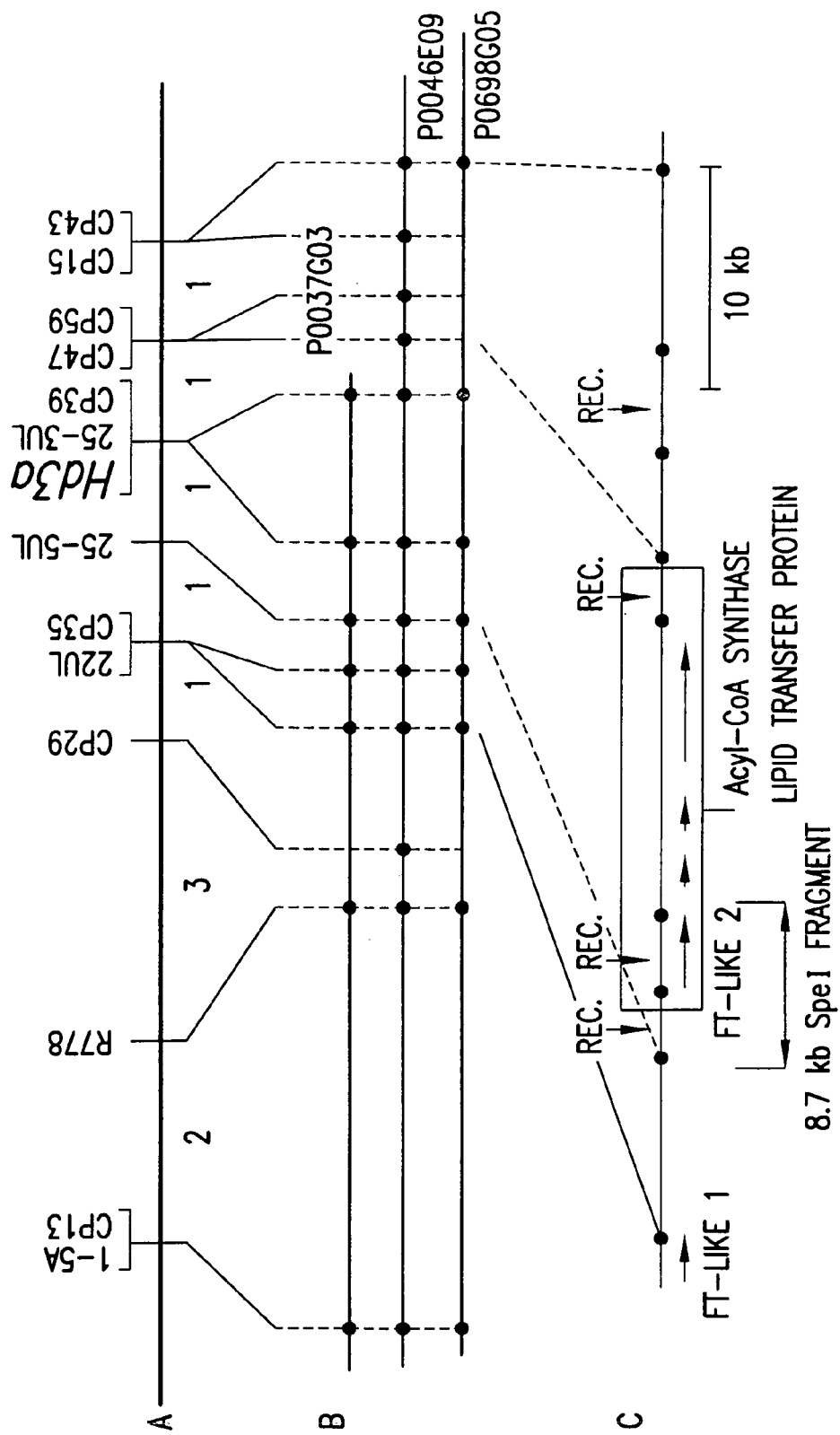
FIG. 1 depicts a diagram showing the high-resolution linkage map of the Hd3a region and candidate genomic region thereof.

A detailed linkage analysis of the Hd3a region with a large segregating population essential for map base cloning was performed. As the segregating population for the linkage analysis, a backcross progeny BC3F3 generation derived from a cross between Nipponbare and Kasalath was used. The linkage analysis was carried out in two steps. First, using 595 plants of the segregating population for the Hd3a region, a linkage map was prepared with RFLP markers. As a result, Hd3a was proven to be localized within the region between the RFLP markers C764 and B174 (Monna, et al., The 1999 Annual Meeting, Japanese Society of Molecular Biology). Then, to further improve the map resolution, linkage analysis was performed with a large population. Specifically, plants having chromosomes in which recombination was occurred in the vicinity of Hd3a were screened from a population of 2207 plants segregated for the Hd3a region using following CAPS (Cleaved Amplified Polymorphic Sequence) markers flanking Hd3a: CP13 (primer [SEQ ID NO: 5/5'-GAGTAATTTGCGGTCAGAGTC-3'] and [SEQ ID NO: 6/5'-CCAAACAACACATCCTCAG-3'], restriction enzyme Tai I)); and CP15 (primer [SEQ ID NO: 7/5'-ACCGCAGGTCTCCTTGTCATT-3'] and [SEQ ID NO: 8/5'-GCTATTGCCATCGCCTTGTGT-3'], restriction enzyme Msp I) The genotype of the Hd3a locus was determined by the progeny testing. Specifically, 10 self-pollinated progeny plants of the selected plants were cultivated in a growth chamber under short-day conditions (irradiation for 10 h) to determine the genotype of Hd3a base on the variation in number of days to heading in each rice line. As a result of the linkage analysis, 8 recombinant plants between Hd3a and CP13, and 2 between Hd3a and CP15 were identified (FIG. 1).

EXAMPLE 2

Alignment of Hd3a Gene Region by P1-derived Artificial Chromosome (PAC) Clones

Three PAC clones (P0037G03, P0046E09, and P0698G05) having the nucleotide sequences of DNA markers 1–5A, R778, and CP39 that are located near the Hd3a locus were screened from the PAC genomic library of Nipponbare. Among the screened 3 PAC clones, P0046E09 and P0698G05 were revealed to have the nucleotide sequences of Hd3a-flanking markers CP13 and CP15, and thus contain the Hd3a gene region (FIG. 1).

EXAMPLE 3

Identification of Candidate Gene Region by Nucleotide Sequence Analysis

To further delimit the candidate genome region of Hd3a and identify the candidate gene, the nucleotide sequence of the PAC clone P0046E09 was analyzed. For the nucleotide sequence analysis, the insert DNA of P0046E09 (including the vector) was ultrasonically fragmented to prepare two sublibraries comprising insert DNAs, one of an average length of 2 kb and the other of 5 kb. Nucleotide sequences of 2000 clones arbitrarily selected from these two types of sublibraries were analyzed and assembled using computer software Phred/Phrap. Using the information on the nucleotide sequences within the candidate gene region specified by the linkage analyses, new CAPS (Cleveland Amplified Polymorphic Sequence) markers were prepared to limit the candidate region. The Hd3a gene co-segregated with CAPS markers 25-3UL (primers [SEQ ID NO: 9/5'-TCAGAACTTCAACACCAAGG-3'] and [SEQ ID NO: 10/5'-ACCTTAGCCTTGCTCAGCTA-3'], restriction enzyme Hae III) and CP39 (primers [SEQ ID NO: 11/5'-GGGAGAATATGTTGCAGTAG-3'] and [SEQ ID NO: 12/5'-CAAATGGTAATGGGTCAA-3'], restriction enzyme Alu I). Furthermore, two plants with recombination were detected, one with a recombination between the Hd3a gene and 25-5UL (primers [SEQ ID NO: 13/5'-CTGTCTCGAAATCGCCTCTG -3'] and [SEQ ID NO: 14/5'-TCCAGCACATCACCCACAA-3'], restriction enzyme Hae III), and the other between the Hd3a and CP59 (primers [SEQ ID NO: 15/5'-AGCCTCTGCGTCACTGTCATC-3'] and [SEQ ID NO: 16/5'-GCAGCAGCAAACTCCCAAAG-3'], restriction enzyme TthH8I), respectively (FIG. 1). Thus, the candidate genomic region was delimited to a region of approximately 20 kb. Gene prediction and similarity search were performed for the nucleotide sequence of this candidate region using GENSCAN, and revealed that detect regions having a very high similarity to genes encoding the lipid transfer protein, acyl-CoA synthase, and FT gene of *Arabidopsis* in the candidate genomic region.

EXAMPLE 4

Expression Analysis of Hd3a Candidate Gene

RT-PCR for the candidate gene was performed for Nipponbare and the nearly isogenic line (NIL (Hd3a)) in which the Hd3a gene region is substituted with a chromosome fragment of Kasalath. Specifically, total RNA was extracted from collected leaves, cDNA was synthesized using reverse transcriptase, and then PCR was performed using primer sets capable of specifically amplifying the 3 genes found within the Hd3a candidate genomic region: (for the FT-like gene: sense strand [SEQ ID NO: 9/5'-TCAGAACTTCAACACCAAGG-3'] and antisense strand [SEQ ID NO: 10/5'-ACCTTAGCCTTGCTCAGCTA-3']; for the lipid transfer protein gene: sense strand [SEQ ID NO: 17/5'-GGGGACGTCGGACCTGT-3'] and antisense strand [SEQ ID NO: 18/5'-AGTTGAAGTTTGGGCTGGTCG-3']; and for the acyl-CoA synthase gene: sense strand [SEQ ID NO: 11/5'-GGGAGAATATGTTGCAGTAG-3'] and antisense strand [SEQ ID NO: 12/5'-CAAATGGTAATGGGTCAA-3']). Assessment of the amount of RNA used as a template was carried out by PCR using a set of primers (sense strand [SEQ ID NO: 19/5'-TCCATCTTGGCATCTCTCAG-3'] and antisense strand [SEQ ID NO: 20/5'-GTACCCGCATCAGGCATCTG-3']) that can amplify a fragment within the actin gene. After cultivating Nipponbare and NIL (Hd3a) for 30 days under long-day conditions (irradiation for 16.0 h), they were further cultivated either under short-day condition (irradiation for 10.0 h) for 0, 2, 6, and 10 days or under the long-day condition for 10 days. Then, leaves were collected from these plants for analysis.

As a result, all of the three predicted genes within the candidate gene region were confirmed to be expressed. The transcript of the FT-like gene was detected in plants cultivated under the short-day condition, but not under the long-day conditions (FIG. 2). No significant difference in the transcript amount was observed between Nipponbare and NIL (Hd3a) under the short-day condition (FIG. 2).

As to other candidate genes, the transcript of lipid transfer protein gene was detected only in Nipponbare, and the transcript of the acyl-CoA synthase gene was detected in both Nipponbare and NIL (Hd3a) but with no difference in the expression level between plants cultivated under the short-day and long-day conditions. According to the aforementioned results, the FT-like gene whose transcription level increases under the short-day condition was used as a potential candidate gene in functional analysis by transformation.

EXAMPLE 5

Nucleotide Sequence Analysis of Hd3a Candidate Gene

A cosmid library was prepared from the genomic DNA of Kasalath to screen clone H3PZ1-1 corresponding to the Hd3a candidate region. More specifically, using the genomic DNA of Kasalath, a genomic DNA library was constructed with the pPZP2CH-lac vector. The library was screened using the nucleotide sequences 25-5UL and CP39 that are in the vicinity of Hd3a to select the clone H3PZ1-1 containing the Hd3a candidate gene (FIG. 1). Nucleotide sequence analysis of the clone and comparison thereof with Hd3a of Nipponbare proved the presence of nucleotide substitution at 32 sites, insertion (2 bp and 3 bp) at 2 sites, and deletion (1 bp to 50 bp) at 7 sites in Nipponbare compared to the Kasalath nucleotide sequence (FIG. 3).

cDNA was synthesized from RNA extracted from a plant of nearly isogenic line (NIL (Hd3a)) for cDNA nucleotide sequence analysis which plant had been treated-under the short-day condition, and RT-PCR was performed using a pair of primers comprising the region from the initiation codon to the termination codon (sense strand [SEQ ID NO: 21/5'-GCTGCCTCTATCACAGTATATT-3'] and antisense strand [SEQ ID NO: 10/5'-ACCTTAGCCTTGCT-CAGCTA-3']). The PCR product was cloned and sequenced. The transcription initiation site was determined by 5'-RACE to confirm that the site was 152 bp upstream of the sequence predicted as the transcription initiation codon.

As a result of the analysis, among the mutations, only a one-nucleotide substitution and a two-nucleotide substitution on the N-terminal side were found to be mutations within the exon. The latter substitution was revealed to cause an amino acid substitution of asparagine (Kasalath) to proline (Nipponbare) (FIG. 3).

EXAMPLE 6

Functional Identification of Candidate Gene by Transformation 8.7 kb SpeI fragment containing only the candidate gene region from the cosmid clone H3PZ1-1 was cloned into vector pPZP2H-lac that can be transformed via Agrobacterium (pPZHd3aK). Similarly, 8.7 kb SpeI fragment of Nipponbare was also incorporated into a pPZP2H-lac (pPZHd3aN). Using the vectors containing these fragments and the vector alone, transformation was performed according to the Toki's method (Plant Mol. Biol. Rep. 15:16–21, 1997). Nipponbare was used as a rice line to be transformed. As a result, 21 (17 with the vector alone) and 20 (20 with the vector alone) hygromycin-resistant plants were obtained in the transformation experiment with pPZHd3aK and pPZHd3aN, respectively.

Whether the intended region had been incorporated was investigated by CAPS analysis with the CAPS marker 25-5UL for pPZHd3aK, and for pPZHd3aN by PCR using primer M13 Primer RV and TAKARA within the vector and the primer within the gene [SEQ ID NO: 22/5'-CGCTCAG-CAACGAGTTTC -3']. As a result, all of the transformants which had been introduced with pPZHd3aK and pPZHd3aN were revealed to have the candidate genes incorporated.

These regenerated plants were immediately transferred into growth chambers set up either for short-day conditions (irradiation for 10 h) or long-day conditions (irradiation for 13.5 h) to investigate the number of days required for heading. Among the plants introduced with pPZHd3aK and pPZHd3aN, plants showing significantly early heading were observed under both the short-day and long-day conditions (Table 1). No plant with any significant changes in the heading time appeared among those introduced with the vector alone (Table 1).

TABLE 1

| | Days till heading[a] | | | | | | | | | | | | | | | | | | | | | | | | |
|---|---|---|---|---|---|---|---|---|---|---|---|---|---|---|---|---|---|---|---|---|---|---|---|---|---|
| | 4 | 8 | 12 | 16 | 20 | 24 | 28 | 32 | 36 | 40 | 44 | 48 | 52 | 56 | 60 | 64 | 68 | 72 | 76 | 80 | 84 | 88 | 92 | 96 | No heading |
| SD pPZHd3aK | | | | 1 | | | 2 | | 4 | 2 | | | | | | | | | | | | | | | |
| Vector alone | | | | | | | | 2 | | 5 | 3 | 1 | | | | | | | | | | | | | |
| LD pPZHd3aK | | | | 1 | | | | | 1 | | 1 | | 1 | 1 | 1 | | 1 | | | | 1 | | | | 4 |
| Vector alone | | | | | | | | | | | | | | | | | | | | | | | | | 6 |
| SD pPZHd3aN | | | 1 | 1 | 2 | 3 | 3 | | | | | | | | | | | | | | | | | | |
| Vector alone | | | | | | | 2 | 3 | 5 | | | | | | | | | | | | | | | | |
| LD pPZHd3aN | | 1 | 1 | | | | 2 | 2 | | | | | | | | | | | | | | 1 | 1 | | 2 |
| Vector alone | | | | | | | | | | | | | | | | | | | | | 1 | 3 | 1 | | 5 |

[a]Days from the transplantation of transformant on soil till heading.
No heading: Plants with no heading within 97 days.
SD and LD: Cultivation under short-day (10.5 h daylight) and long-day (13.5 h daylight) conditions, respectively.
pPZHd3aK and pPZHd3aN: Vectoes inserted with Hd3a genes of Kasalath and Nipponbare, respectively.

Furthermore, when the self-pollinated progeny from the early-heading transformed plant (pPZHd3aK) was cultivated under the short-day condition to examine the segregation in the number of days to heading, the variation was in a continuous distribution, but plants showing early heading compared to the control Nipponbare were segregated and the segregated plants contained the transgene (FIG. 4A).

On the other hand, when self-pollinated progenies were similarly cultivated under the long-day conditions, heading plants appeared among these progenies in contrast to Nipponbare and NIL (Hd3a) for which no heading is observed even after 100 days. All of the heading plants contained the introduced DNA fragments (FIG. 4B).

These results confirmed that the FT-like gene, i.e., the candidate gene, has the function to promote the heading under the short-day conditions, and the gene was determined to be the Hd3a. The heading action of the allele of Kasalath was predicted to be stronger than that of Nipponbare. However, the allele of Nipponbare was also suggested to maintain the function to a degree. Early heading observed under the long-day conditions is likely to occur due to the elevated Hd3a expression level via the newly introduced Hd3a gene by transformation.

INDUSTRIAL APPLICABILITY

The present invention provides genes that induce the flowering of plant. The present invention makes it possible to control the heading date of rice, and thus may be very useful inbreeding. Control of the heading date of rice plants is particularly useful for breeding rice cultivars adapted to particular locations and seasons. Furthermore, the method for breeding rice cultivars using a gene of the present invention is beneficial as compared to conventional methods, in that an object plant can be obtained in a short period with high reliability.

The invention claimed is:

1. An isolated DNA encoding a protein derived from plants which induces the flowering of plants, wherein said DNA is selected from the group consisting of:
    (a) a DNA encoding the protein comprising the amino acid sequence of SEQ ID NO: 2; and
    (b) a DNA encoding the protein comprising the amino acid sequence of SEQ ID NO: 2, wherein one amino acid is substituted, deleted, added, and/or inserted.

2. The DNA of claim 1, wherein the DNA is derived from rice.

3. The DNA of claim 1, wherein the DNA is used to induce the flowering of a plant.

4. A vector comprising the DNA of claim 1.

5. A plant cell transformed with the vector of claim 4.

6. A plant transformant comprising the plant cell of claim 5.

7. The plant transformant of claim 6, wherein said plant transformant is rice.

8. A plant transformant, which is a progeny or a clone of the plant transformant of claim 6 and comprises an isolated DNA encoding a protein derived from plants which induces the flowering of plants, wherein said DNA is selected from the group consisting of:
  (a) a DNA encoding the protein comprising the amino acid sequence of SEQ ID NO:2; and
  (b) a DNA encoding the protein comprising the amino acid sequence of SEQ ID NO:2, wherein one amino acid is substituted, deleted, added, and/or inserted.

9. A breeding material of the plant transformant of claim 6, which comprises an isolated DNA encoding a protein derived from plants which induces the flowering of plants, wherein said DNA is selected from the group consisting of:
  (a) a DNA encoding the protein comprising the amino acid sequence of SEQ ID NO:2; and
  (b) a DNA encoding the protein comprising the amino acid sequence of SEQ ID NO:2, wherein one amino acid is substituted, deleted, added, and/or inserted.

10. A method for producing a plant transformant, which comprises the following steps of:
  (a) introducing the DNA of claim 1 into a plant cell, and
  (b) regenerating a plant from the plant cell.

11. A method for inducing the flowering of a plant, comprising:
  (a) introducing the DNA of claim 1 into a plant cell, and
  (b) regenerating a plant from the plant cell
  and wherein said DNA is expressed and flowering is induced.

12. The method of claim 10, wherein the plant is rice.

\* \* \* \* \*